(12) United States Patent
Okabe et al.

(10) Patent No.: US 7,554,048 B2
(45) Date of Patent: Jun. 30, 2009

(54) ULTRASONIC TREATMENT SWITCH DEVICE AND MEDICAL DEVICE SWITCH ATTACHMENT SYSTEM

(75) Inventors: Hiroshi Okabe, Hachioji (JP); Yoshitaka Fujii, Atsugi (JP)

(73) Assignee: Olympus Medical Systems Corporation (JP)

( * ) Notice: Subject to any disclaimer, the term of this patent is extended or adjusted under 35 U.S.C. 154(b) by 493 days.

(21) Appl. No.: 11/446,879

(22) Filed: Jun. 5, 2006

(65) Prior Publication Data

US 2007/0013992 A1    Jan. 18, 2007

(30) Foreign Application Priority Data

Jun. 8, 2005    (JP)    ............................... 2005-168268

(51) Int. Cl.
*H01H 9/06*    (2006.01)
(52) U.S. Cl. .................................... 200/332.2; 200/341
(58) Field of Classification Search ......... 200/310–314, 200/341–345, 332.2
See application file for complete search history.

(56) References Cited

U.S. PATENT DOCUMENTS 5,033,326 A * 7/1991 Powell et al. ............... 74/551.4
5,376,089 A * 12/1994 Smith .......................... 606/42
6,325,795 B1 * 12/2001 Lindemann et al. ........... 606/32

FOREIGN PATENT DOCUMENTS

JP    2003-70800    3/2003

* cited by examiner

*Primary Examiner*—Michael A Friedhofer
*Assistant Examiner*—Lisa N Klaus
(74) *Attorney, Agent, or Firm*—Ostrolenk, Faber, LLP

(57) ABSTRACT

An ultrasonic treatment switch device includes an adapter, a switch, a switch fixing portion and an adapter fixing portion. The adapter is connected to a power source and having a hand piece fixing portion detachably attached to a hand piece having an ultrasonic transducer. The switch is connected to the power source and causes an electric signal to be output from the power source so that the ultrasonic transducer generates ultrasonic vibrations. The switch fixing portion is provided in the switch and detachably attached to the adapter. The adapter fixing portion is provided in the adapter. The switch fixing portion is attached to the adapter fixing portion.

11 Claims, 7 Drawing Sheets

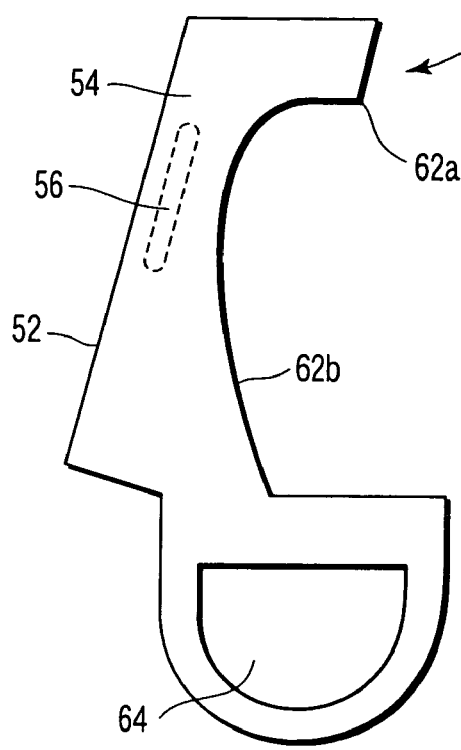 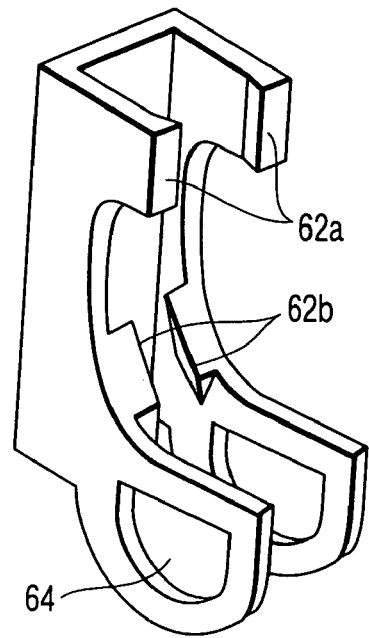
F I G. 4A   F I G. 4B
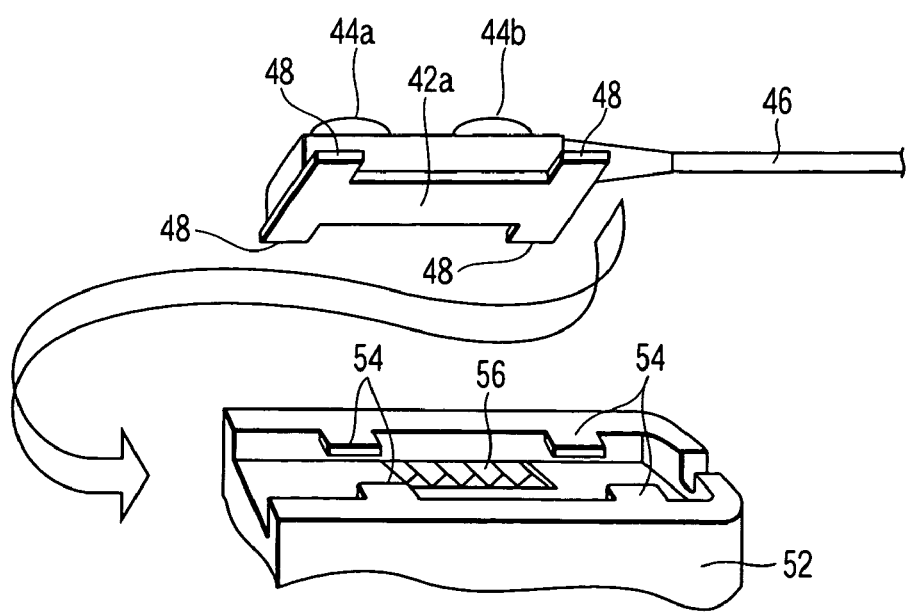
F I G. 5

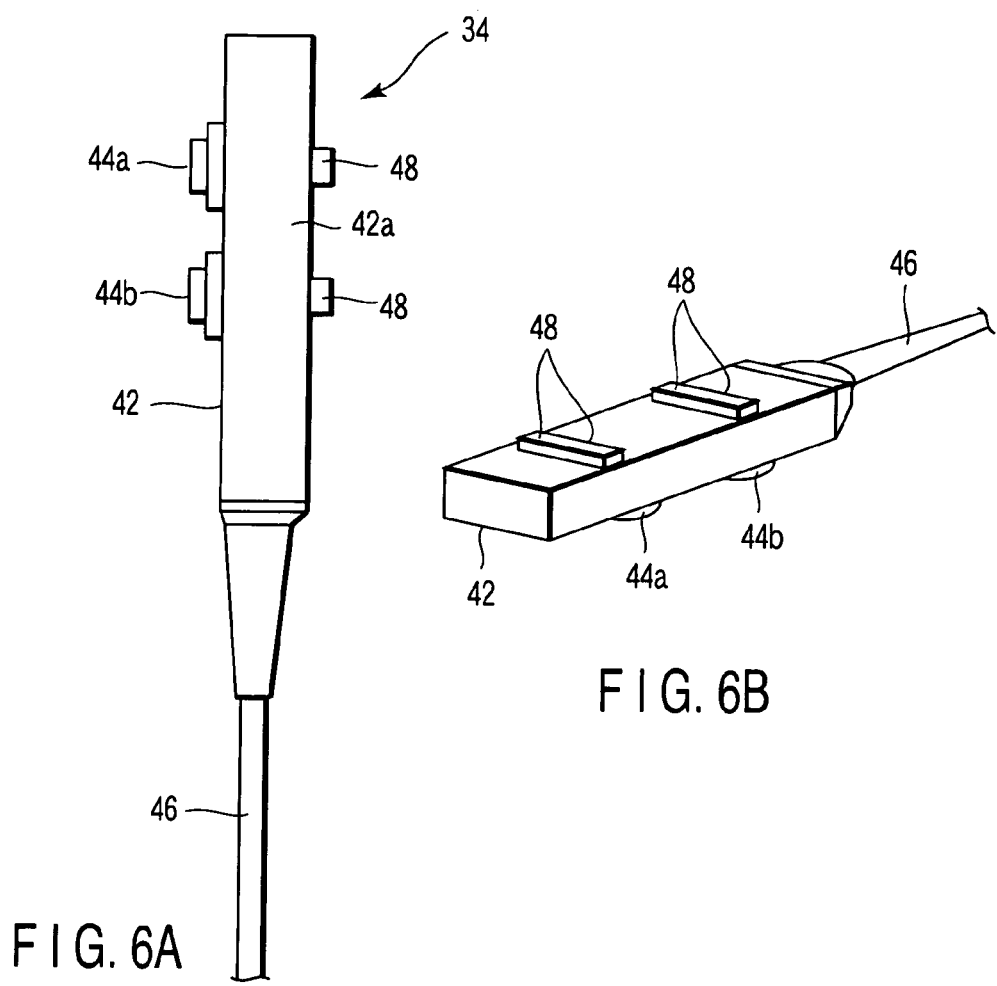
FIG. 6A
FIG. 6B
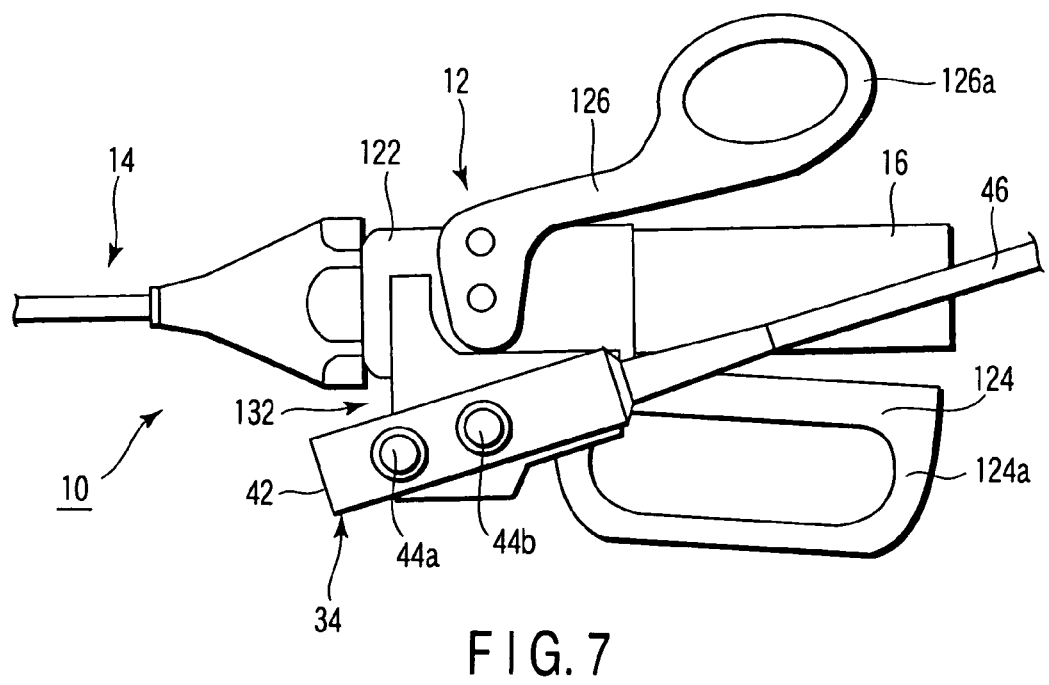
FIG. 7

ULTRASONIC TREATMENT SWITCH DEVICE AND MEDICAL DEVICE SWITCH ATTACHMENT SYSTEM

CROSS-REFERENCE TO RELATED APPLICATIONS

This application is based upon and claims the benefit of priority from prior Japanese Patent Application No. 2005-168268, filed Jun. 8, 2005, the entire contents of which are incorporated herein by reference.

BACKGROUND OF THE INVENTION

1. Field of the Invention

The present invention relates to an ultrasonic treatment switch device disposed in an ultrasonic treatment apparatus and manually operated and to a medical device switch attachment system.

2. Description of the Related Art

For example, Jpn. Pat. Appln. KOKAI Publication No. 2003-70800 has disclosed a hand switch for high-frequency cautery. This hand switch comprises a cord connection portion to which a conducting cord extending from a high-frequency power source main body can be connected, and this conducting cord conducts a high-frequency current to a distal end of a probe to achieve high-frequency incision and high-frequency coagulation of a tissue in turn. Such a hand switch is detachably disposed in a sheath of an ultrasonic suction device owing to the elastic force of a resin material.

BRIEF SUMMARY OF THE INVENTION

According to an aspect of the present invention, an ultrasonic treatment switch device includes an adapter, a switch, a switch fixing portion and an adapter fixing portion. The adapter is connected to a power source and having a handpiece fixing portion detachably attached to a handpiece having an ultrasonic transducer. The switch is connected to the power source and causes an electric signal to be output from the power source so that the ultrasonic transducer generates ultrasonic vibrations. The switch fixing portion is provided in the switch and detachably attached to the adapter. The adapter fixing portion is provided in the adapter. The switch fixing portion is attached to the adapter fixing portion.

According to an aspect of the present invention, a medical device switch attachment system includes an adapter and a hand switch. The adapter is detachably attached to a medical device gripped and used by a user. The hand switch is detachably attached to the adapter. The hand switch is disposed at a position within reach of the user while the medical device is gripped by the user, and switches the operation of the medical device. The adapter includes a common fixing seat and a medical device attachment/detachment portion. The hand switch is attached to the fixing seat. The medical device attachment/detachment portion is formed in conformity to the medical device.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4A is a schematic side view showing the fixed handle adapter in the ultrasonic treatment switch device according to the first embodiment;

FIG. 4B is a schematic perspective view showing the fixed handle adapter in the ultrasonic treatment switch device according to the first embodiment when observed obliquely from above;

FIG. 5 is a schematic perspective view showing how the switch unit in the ultrasonic treatment switch device according to the first embodiment is attached to the fixed handle adapter when observed obliquely from above;

FIG. 6A is a schematic side view showing a modification of the switch unit in the ultrasonic treatment switch device according to the first embodiment;

FIG. 6B is a schematic perspective view showing the modification of the switch unit in the ultrasonic treatment switch device according to the first embodiment when observed from a bottom side;

FIG. 7 is a schematic side view showing how the switch unit and an in-line adapter in an ultrasonic treatment switch device according to a second embodiment are attached to a medical ultrasonic handpiece;

DETAILED DESCRIPTION OF THE INVENTION

A best mode for carrying out this invention will hereinafter be described with reference to the drawings.

A first embodiment will be described with FIGS. 1 to 5.

Figure 1:
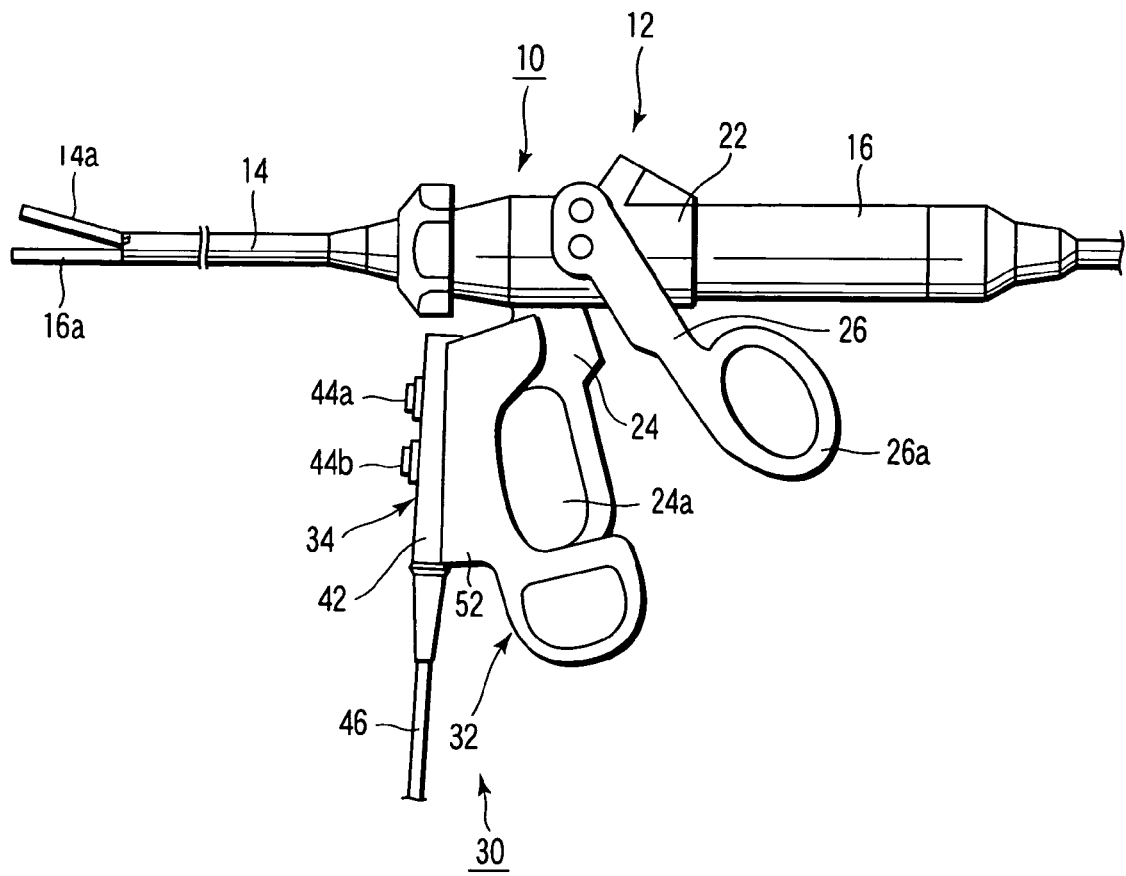
FIG. 1 is a schematic side view showing how a switch unit and a fixed handle adapter in an ultrasonic treatment switch device according to a first embodiment are attached to a medical ultrasonic handpiece.

A medical ultrasonic handpiece (medical device) 10 shown in FIG. 1 converts electric power supplied from a power source main body into ultrasonic vibrations (vibration energy) by an ultrasonic transducer 16. Then, the ultrasonic vibrations generated in the ultrasonic transducer 16 are transmitted from a proximal end of a probe 16a connected to the ultrasonic transducer 16 to a distal end thereof while the vibration energy is being amplified.

As shown in FIG. 1, the medical ultrasonic handpiece 10 includes a handle portion 12, an insertion portion 14 extending from the handle portion 12 to a distal end thereof, and the ultrasonic transducer 16 attached to a proximal end of the handle portion 12. The insertion portion 14 includes at its distal end an open/close portion (jaw) 14a openable/closable by the operation of the handle portion 12. Thus, if the ultrasonic vibrations are provided to the probe 16a while a treatment target is put between the distal end of the probe 16a connected at its proximal end to the ultrasonic transducer 16 and the open/close portion 14a, the treatment target is subjected to ultrasonic treatment.

The handle portion 12 includes an operation main body 22 having a fixed handle 24, and a movable handle 26 pivotally supported on the operation main body 22 and openable/closable with respect to the fixed handle 24. The fixed handle 24 is formed substantially perpendicularly to the axial direction of the insertion portion 14. Therefore, this medical ultrasonic handpiece 10 is formed substantially to be a general pistol type. Further, the open/close portion 14a is opened/closed in conjunction with the operation of the movable handle 26 with respect to the fixed handle 24.

Finger hook portions 24a and 26a are formed in the fixed handle 24 and the movable handle 26, respectively. The thumb of the right or left hand of a user is put into the finger hook portion 26a of the movable handle 26. The forefinger, middle finger or the like of the right or left hand of the user is put into the finger hook portion 24a of the fixed handle 24.

The fixed handle 24 is provided with an ultrasonic treatment switch device (medical device switch attachment system, ultrasonic treatment device hand switch apparatus) 30. This switch device 30 includes a fixed handle adapter (switch unit adapter) 32 detachably attached to the fixed handle 24, and a switch unit (hand switch) 34 detachably attached to the adapter 32. The adapter 32 fixes the handpiece 10 and the switch unit 34 within a specified range. The switch unit 34 detects a signal from the power source main body to control turning an ultrasonic output on or off.

Figure 2A:
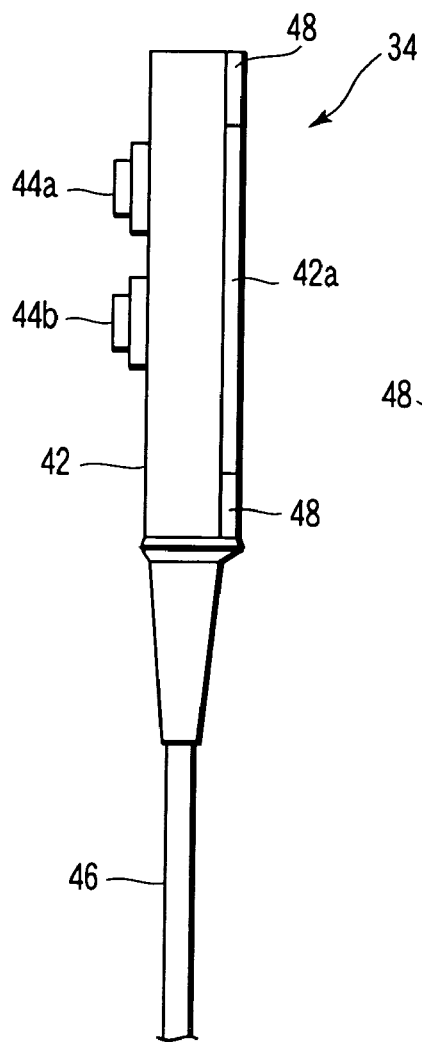
FIG. 2A is a schematic side view showing the switch unit in the ultrasonic treatment switch device according to the first embodiment.
Figure 2B:
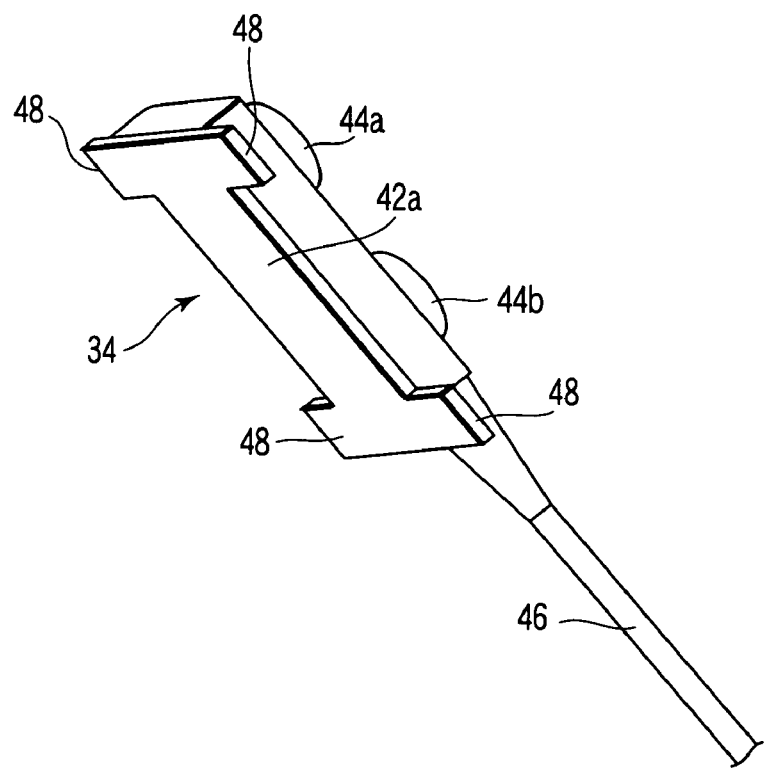
FIG. 2B is a schematic perspective view showing the switch unit in the ultrasonic treatment switch device according to the first embodiment when observed from a bottom side.

As shown in FIGS. 2A and 2B, the switch unit 34 includes a substantially box-type switch main body 42 which is for example, flat and elongated, press buttons 44a and 44b disposed in the switch main body 42, a cable 46 extending from the switch main body 42, and fixing claws (switch fixing portions) 48 which are disposed in the switch main body 42 and which can be fitted into the fixed handle adapter 32. The cable 46 is connected to the unshown power source main body in the same manner as the ultrasonic transducer 16. Thus, the cable 46 communicates a signal line electrically connected to the power source main body with the inside of the switch main body 42.

The press buttons 44a and 44b are disposed side by side on one side of the switch main body 42. Of the press buttons 44a and 44b, the one press button 44a, for example, turns a detected current from the power source main body (not shown) on or off to control the turning on or off of the ultrasonic output from the ultrasonic transducer 16. Here, the ultrasonic output is in an on-state when the press button 44a is, for example, pressed, while the ultrasonic output is in an off-state when the press button 44a is unpressed (untouched). The other press button 44b changes the intensity of the output from the ultrasonic transducer 16, or, although not shown in the drawings, switches on or off a high-frequency output which can be input from the side of the probe 16a by the handpiece 10. Thus, if the press buttons 44a and 44b are pressed or untouched, a current to the ultrasonic transducer 16 and the like can be passed or shut off.

A plurality of fixing claws 48 is formed on a bottom 42a of the main body 42. The fixing claws 48 are formed in a flange shape at one and the other ends of the bottom 42a symmetrically with respect to the longitudinal direction of the bottom 42a. The fixing claws 48 fit into a later-described fixing projections 54 of the adapter 32, and are thus used to position the switch unit 34 with respect to the fixed handle adapter 32.

Figure 3:
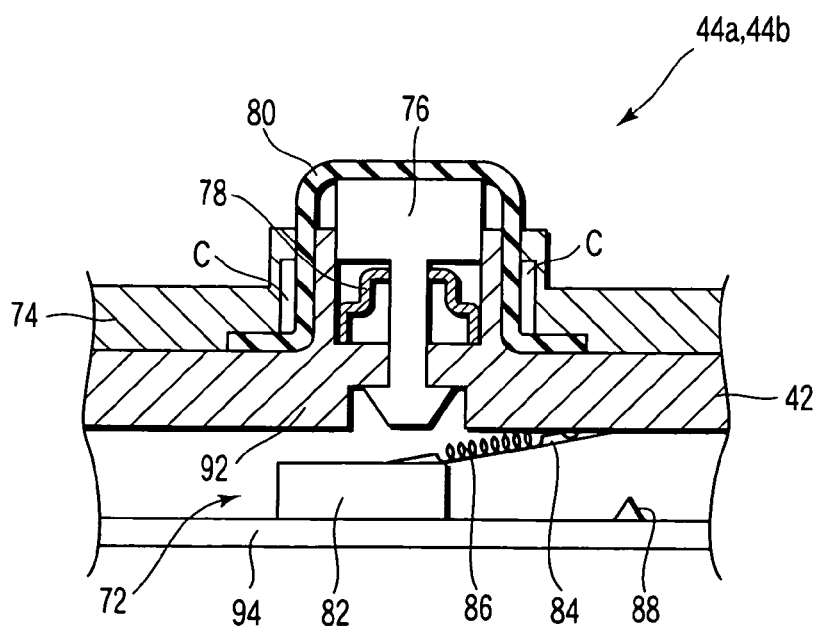
FIG. 3 is a schematic perspective view showing a tactile switch disposed in the switch unit in the ultrasonic treatment switch device according to the first embodiment.

As shown in FIG. 3, the press button 44a, 44b of the switch unit 34 includes a tactile switch 72 and a cover fixing lid 74. The cover fixing lid 74 is disposed on the surface of the main body 42, and fixes the tactile switch 72. That is, the cover fixing lid 74 fixes a later-described rubber cover 80 to the main body 42.

The tactile switch 72 includes an operation pin 76, a packing 78, the rubber cover 80, a support table 82, a plate member 84, a spring 86 and a contact 88.

A cylindrical button frame 92 is formed in the main body 42. A through-hole is formed at the central axis of the button frame 92. The operation pin 76 is disposed in the button frame 92. The operation pin 76 is disposed movably in a direction perpendicular to the main body 42 owning to the button frame 92. The operation pin 76 is urged to the outside of the main body 42 by the packing 78 whose one end is disposed in the main body 42 and whose other end is disposed in the operation pin 76. That is, while keeping the operation pin 76 and the main body 42 watertight, the packing 78 presses (urges) the operation pin 76 to the outside of the main body 42 when the press buttons 44a and 44b are untouched. Such a packing 78 makes it possible to keep a pair of switch sections inside the press buttons 44a and 44b watertight and vapor-tight.

The rubber cover 80 is disposed outside the operation pin 76 and the button frame 92. This rubber cover 80 is fixed to the main body 42 by the cover fixing lid 74. Therefore, the inside of the operation pin 76 is kept watertight by the rubber cover 80. That is, the inside of the operation pin 76 is kept watertight by the rubber cover 80 and the packing 78.

A clearance C is formed between the cover fixing lid 74 and the rubber cover 80. This clearance C is an escape for a deformed part of rubber when the rubber cover 80 presses the operation pin 76 against the urging force of the packing 78. This allows good operability to be maintained when the press buttons 44a and 44b are pressed.

In this embodiment, the two press buttons 44a and 44b are provided. In this case, it is preferable that the press buttons 44a and 44b have different feels and sizes so that it is possible to readily recognize which of the press buttons 44a and 44b is to be used.

The support table 82 serves as a base for a switch, and is fixed to a substrate 94. This substrate 94 is electrically connected to the signal line in the cable 46. Thus, the substrate 94 is electrically conducted to the power source main body. The support table 82 positions the contact 88. The plate member 84 is pressed down and contacts the contact 88 when the operation pin 76 is pressed. Then, the contact 88 is electrically conducted to the substrate 94.

The spring 86 urges the plate member 84 so that the plate member 84 is always in contact with an inner peripheral surface of the main body 42. If the press buttons 44a and 44b are not pressed against the urging force of the packing 78, the contact 88 and the plate member 84 are always separated. The contact 88 is electrically conducted when the plate member 84 contacts the contact 88.

As shown in FIGS. 4A and 4B, the fixed handle attachment adapter 32 includes a switch unit fixing seat (adapter fixing portion) 52 made of a plastic material to position the switch main body 42. As shown in FIG. 5, one side of this fixing seat 52 is used to attach the switch unit 34. As shown in FIG. 1, the other side of the fixing seat 52 is used to be attached to the fixed handle 24 of the handpiece 10.

As shown in FIGS. 4A and 5, in the fixing seat 52, there are formed the fixing projections 54 and a switch unit fixing rubber member 56. The switch unit fixing claws 48 of the switch main body 42 fit into the fixing projections 54. The fixing projections 54 are arranged symmetrically with respect to the direction in which the switch unit 34 is attached. Further, as shown in FIG. 5, the fixing rubber member 56 arranges the fixing projections 54 and the fixing claws 48 so that they are pressed against each other by the elastic force of the rubber. Thus, the fixing rubber member 56 of the adapter 32 uses frictional force between this fixing rubber member 56 and the bottom 42a of the main body 42 of the switch unit 34 to regulate the sliding of the switch unit 34 over the adapter 32 during use. Moreover, the fixing rubber member 56 of the adapter 32 prevents movement produced between the switch unit 34 and the adapter 32. In the switch unit 34 and the fixed handle attachment adapter 32, the fixing claws 48 are disposed inside the fixing projections 54 when the fixing claws 48 fit into the fixing projections 54.

As shown in FIG. 4B, on the other side of the fixing seat 52, there are formed pairs of fixing hooks (medical device attachment/detachment portions) 62a and 62b to be fixed to the fixed handle 24, and a pair of operating insertion portions (hook portions) 64, in conformity to the fixed handle 24 so that the fixed handle 24 is held between those pairs.

The fixing hooks 62a are formed at upper ends on the rear surface of the fixing seat 52. The fixing hooks 62a are formed to be opposite to each other. Moreover, the fixing hooks 62b are formed at lower ends on the rear surface of the fixing seat 52. The fixing hooks 62b are formed to be opposite to each other in the same manner as the above-mentioned fixing hooks 62a. Thus, the fixing hooks 62a and 62b cause the adapter 32 to be fitted into and fixed to the fixed handle 24 of the handpiece 10 by the elasticity of the plastic material when attaching the adapter 32 to the fixed handle 24 of the handpiece 10.

The operating finger insertion portions 64 are formed at lower ends of the fixing hooks 62b. The third or little finger of the user is put in the finger insertion portions 64 in use. If the third or little finger of the user is put in the finger insertion portions 64 when the fixed handle 24 is attached, the finger insertion portions 64 increase the freedom in gripping the handpiece 10, for example, the finger insertion portions 64 can increase the movable range of the forefinger. That is, the user selects how to grip the handle portion 12 and the adapter 32.

Next, the function of the ultrasonic treatment switch device 30 according to this embodiment will be described.

The switch unit 34 is attached to the fixed handle attachment adapter 32. At this moment, the bottom 42a of the main body 42 of the switch unit 34 is slid over the fixing seat 52 of the adapter 32. Then, the fixing claws 48 of the bottom 42a of the main body 42 are engaged with the fixing projections 54 of the fixing seat 52 of the adapter 32. Thus, the fixing rubber member 56 of the adapter 32 is mechanically pressed against and fixed to the bottom 42a of the main body 42. That is, the switch unit 34 is attached to the adapter 32.

The fixed handle attachment adapter 32 mounted with the switch unit 34 is attached to the fixed handle 24 of the handpiece 10. At this moment, the fixing hooks 62a and 62b of the adapter 32 are engaged with the fixed handle 24. In this adapter 32, the operating finger insertion portions 64 into which the finger can be inserted are disposed in parallel in addition to the finger hook portion 24a of the fixed handle 24, thereby making it possible to operate the press buttons 44a and 44b of the switch unit 34 with the forefinger of the right or left hand in a freer state.

As described above, the following can be said according to this embodiment.

One part (one side) of the adapter 32 is formed in a shape attachable to/detachable from the switch unit 34, so that if the other part (the other side) of the adapter 32 is formed in conformity to the shape of, for example, the handpiece 10, the switch unit 34 can be in common use. That is, if the kind of medical ultrasonic handpiece 10 is not specified and the adapter 32 exclusive to that handpiece 10 is prepared, it is possible to provide the ultrasonic treatment switch device 30 in which the press buttons 44a and 44b are easily operated.

The switch unit 34 can be placed in the adapter 32 within a predetermined range. That is, the press buttons 44a and 44b of the switch unit 34 can be placed at positions where they can be easily pressed. Thus, the operability of the switch unit 34, that is, the press buttons 44a and 44b, can be enhanced. Even if operating time (pressing time) is long, it is possible to keep pressing the press buttons 44a and 44b without easily getting tired with a moderate amount of pressure and press stroke. Since the press buttons 44a and 44b are disposed at the positions where they can be easily operated, it is possible to minimize effects of hand movement in the probe 16a and at the distal end of the open/close portion 14a.

In the embodiment described above, the switch unit fixing claws 48 of the flange shape are provided at one and the other ends of the bottom 42a of the main body 42, but it is also preferable that the fixing claws 48 are protrusively formed as shown in FIGS. 6A and 6B. In this case, the fixing rubber member 56 is formed in a slotted shape. Then, the fixing claws 48 and the fixing rubber member 56 are fixed in a mechanically pressed state.

Next, a second embodiment will be described with FIGS. 7 to 8B. This embodiment is a modification of the first embodiment, so that the same signs are assigned to the same members as those described in the first embodiment and those members are not described in detail.

As shown in FIG. 7, in the medical handpiece 10 according to this embodiment, the handle portion 12 is formed to be an in-line type, in contrast with the handle portion in the medical handpiece 10 (see FIG. 1) described in the first embodiment. This handle portion 12 includes an operation main body 122 having a fixed handle 124, and a movable handle 126 pivotally supported on the operation main body 122 and openable/closable with respect to the fixed handle 124. The fixed handle 124 is disposed along the axial direction of the insertion portion 14. Therefore, this medical ultrasonic handpiece 10 is formed to be the scissors-shaped in-line type in which an open/close knob horizontally opens with respect to the long axis of the insertion portion 14. Further, the open/close portion 14a is opened/closed in conjunction with the operation of the movable handle 126 with respect to the fixed handle 124. It is to be noted that finger hook portions 124a and 126a are formed in the fixed handle 124 and the movable handle 126, respectively. The thumb of the right or left hand of the user is put into the finger hook portion 126a of the movable handle 126. The forefinger, middle finger or the like of the right or left hand of the user is put into the finger hook portion 124a of the fixed handle 124.

Figure 8A:
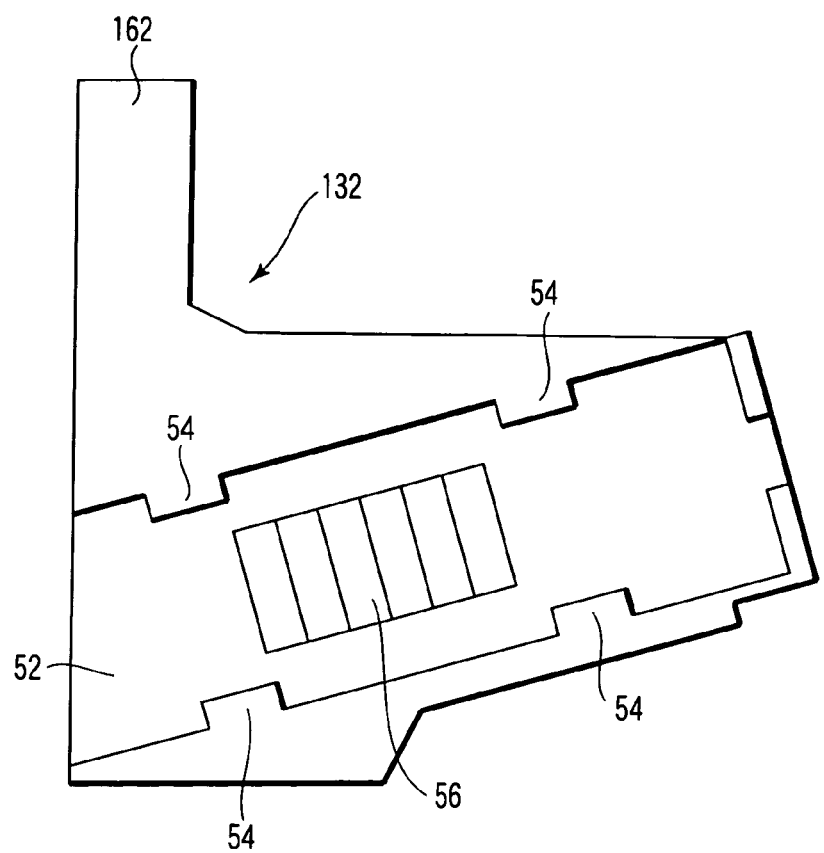
FIG. 8A is a schematic side view showing the in-line adapter in the ultrasonic treatment switch device according to the second embodiment.

An in-line adapter 132 is detachably attached to the operation main body 122. As shown in FIG. 8B, the in-line adapter 132 includes a pair of switch unit fixing seats 52 to position the switch main body 42. A pair of (two) fixing seats 52 is provided to be able to accommodate both right-handedness and left-handedness. As shown in FIGS. 8A and 8B, in the fixing seats 52, there are formed the fixing projections 54 and the switch unit fixing rubber member 56, in the same manner as the fixing seat 52 (see FIG. 5) described in the first embodiment.

The switch unit fixing claws 48 of the switch main body 42 fit into the fixing projections 54. As shown in FIG. 5, the fixing rubber member 56 arranges the fixing projections 54 and the fixing claws 48 so that they are pressed against each other by the elastic force of the rubber. Thus, the fixing rubber member 56 of the adapter 32 uses the frictional force between this fixing rubber member 56 and the bottom 42a of the main body 42 of the switch unit 34 to regulate the sliding of the switch unit 34 over the adapter 32 during use.

Figure 8B:
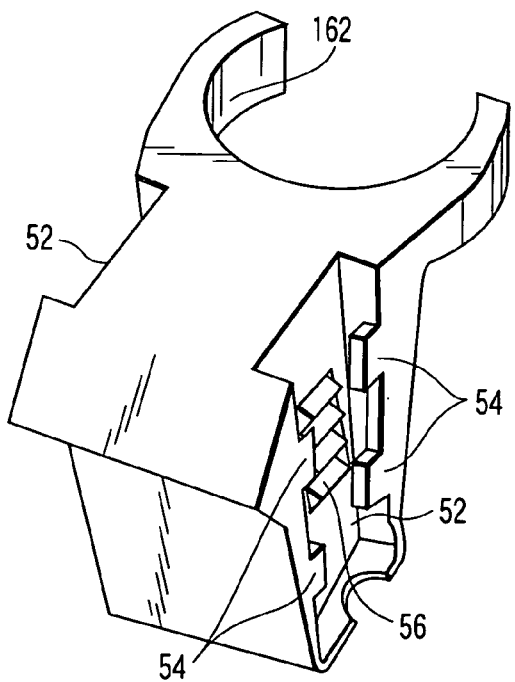
FIG. 8B is a schematic perspective view showing the in-line adapter in the ultrasonic treatment switch device according to the second embodiment when observed obliquely from above.

As shown in FIGS. 8A and 8B, fixing hooks (medical device attachment/detachment portions) 162 to be fixed to the main body 122 are formed in the fixing seats 152. The fixing hooks 162 extend in an arm shape. The shape of the hooks 162 is formed to be smaller than the outer peripheral surface of the main body 122 in order to hold the main body 122. An angle between the extending direction of the fixing hooks 162 and the longitudinal direction of the fixing seats 152 is formed smaller than 90 degrees.

Next, the function of the ultrasonic treatment switch device 30 according to this embodiment will be described.

The switch unit 34, the in-line adapter 132 and the handpiece 10 are combined together.

The fixing hooks 162 of the adapter 132 are attached to the main body 122. In this case, since the hooks 162 are formed of a plastic material, they elastically deform, and are thus wound around and attached to the main body 122.

At this moment, the fixing hooks 162 are placed in the main body 122 in a state slightly inclined with respect to the longitudinal direction thereof in such a manner as to establish a positional relationship whereby the switch unit 34 is held in the palm and to allow the press buttons 44a and 44b to be operated with the forefinger in a freer state. Because the switch unit 34 includes two switch unit fixing seats 52, it can be disposed on any one of the right and left sides of the movable handle 126.

As described above, the following can be said according to this embodiment.

Since the adapter 132 includes a pair of fixing seats 52, the switch unit 34 can be disposed on the side desired by the user. Thus, it is possible to enhance the operability of, for example, the press buttons 44a and 44b of the switch unit 34.

Next, a third embodiment will be described with FIGS. 9 to 10B. This embodiment is a modification of the first and second embodiments, so that the same signs are assigned to the same members as those described in the first and second embodiments and those members are not described in detail.

Figure 9:
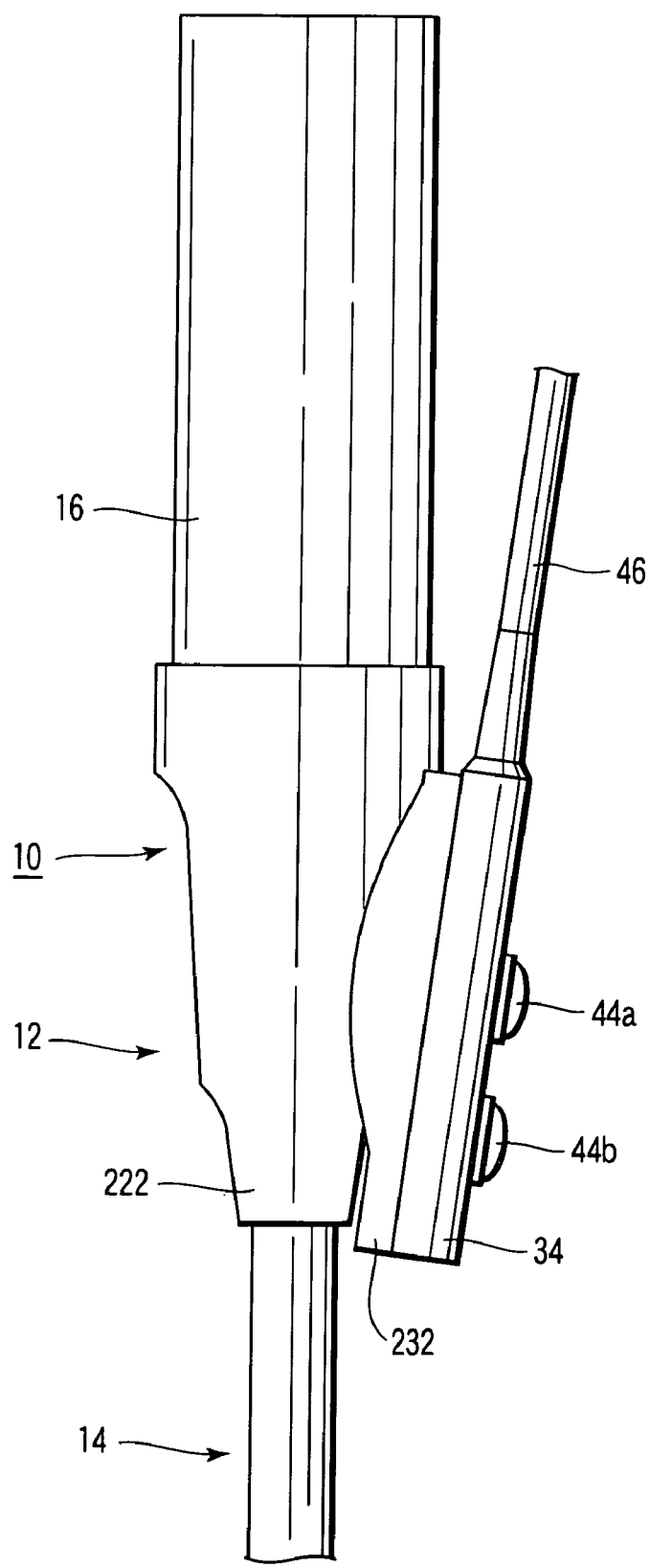
FIG. 9 is a schematic side view showing how the switch unit and a hook adapter in an ultrasonic treatment switch device according to a third embodiment are attached to the medical ultrasonic handpiece.

As shown in FIG. 9, in the substantially pencil-shaped medical handpiece 10 according to this embodiment, the handle portion 12 is formed to be a hook type, in contrast with the handle portion in the medical handpieces 10 (see FIGS. 1 and 7) described in the first and second embodiments. This handle portion 12 includes an operation main body 222.

Figure 10A:
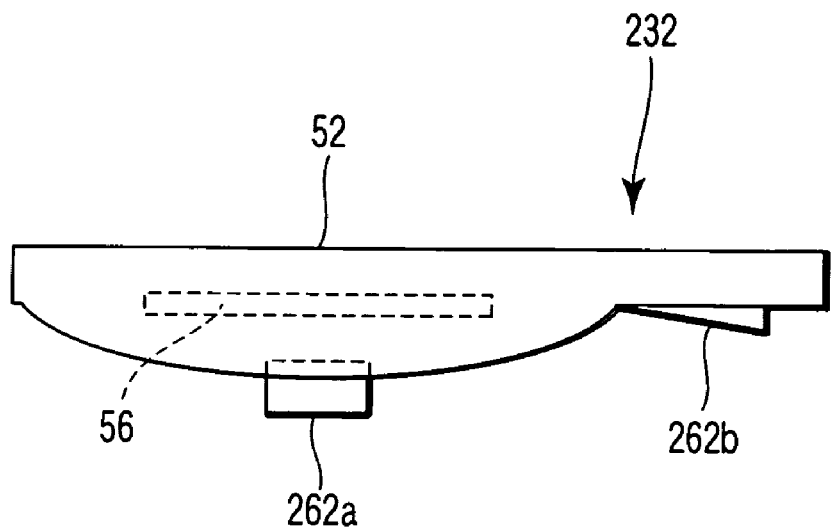
FIG. 10A is a schematic side view showing the hook adapter in the ultrasonic treatment switch device according to the third embodiment.

A hook adapter 232 is detachably attached to the operation main body 222. As shown in FIGS. 10A and 10B, the hook adapter 232 includes the switch unit fixing seat 52 to position the switch main body 42. In this fixing seat 52, there are formed the fixing projections 54 and the switch unit fixing rubber member 56, in the same manner as the fixing seat 52 (see FIG. 5) described in the first and second embodiments.

The switch unit fixing claws 48 of the switch main body 42 fit into the fixing projections 54. As shown in FIG. 5, the fixing rubber member 56 arranges the fixing projections 54 and the fixing claws 48 so that they are pressed against each other by the elastic force of the rubber. Thus, the fixing rubber member 56 of the adapter 232 uses the frictional force between this fixing rubber member 56 and the bottom 42a of the main body 42 of the switch unit 34 to regulate the sliding of the switch unit 34 over the adapter 232 during use.

Figure 10B:
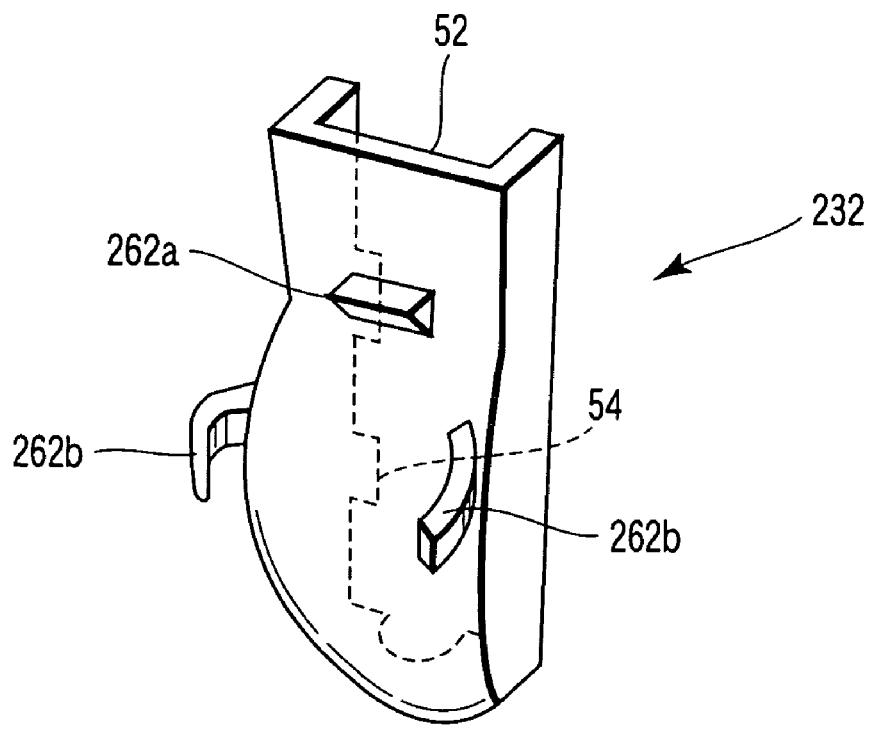
FIG. 10B is a schematic perspective view showing the hook adapter in the ultrasonic treatment switch device according to the third embodiment when observed obliquely from above.

As shown in FIGS. 10A and 10B, fixing hooks (medical device attachment/detachment portions) 262a and 262b to be fixed to the main body 222 are formed in the fixing seat 52. A pair of fixing hooks 262b is formed. The fixing hooks 262a and 262b are engaged with unshown engaging portions of the main body 222.

Next, the function of the ultrasonic treatment switch device 30 according to this embodiment will be described.

The switch unit 34, the hook adapter 232 and the hook type handpiece 10 are combined together.

The fixing hooks 262a and 262b of the adapter 232 are attached to the main body 222. In this case, the adapter 232 is attached to the main body 222 while being slid over a surface thereof having the fixing hooks 262a and 262b.

Furthermore, as in the first embodiment, the switch unit 34 is attached to the adapter 232. At this moment, the press buttons 44a and 44b are disposed at positions where they can be easily pressed.

As described above, the following can be said according to this embodiment.

The handpiece 10 is substantially pencil-shaped, and the switch unit 34 is attached to the handle portion 12 of the handpiece 10 via the adapter 232, so that the press buttons 44a and 44b of the switch unit 34 can be easily operated.

The ultrasonic handpiece 10 is used in the first to third embodiments described above, but the present invention is also suitably applicable to other medical devices using hand switches.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An ultrasonic treatment switch device comprising:
   an adapter connected to a power source and having a handpiece fixing portion detachably attached to a handpiece having an ultrasonic transducer;
   a switch which is connected to the power source and which causes an electric signal to be output from the power source so that the ultrasonic transducer generates ultrasonic vibrations;
   a switch fixing portion provided in the switch and detachably attached to the adapter; and
   an adapter fixing portion which is provided in the adapter and to which the switch fixing portion is attached.

2. The ultrasonic treatment switch device according to claim 1, wherein the adapter fixing portion and the switch fixing portion are provided substantially symmetrically to the adapter and the switch, respectively.

3. The ultrasonic treatment switch device according to claim 1, wherein the adapter is provided with a movement prevention member which prevents mutual movement when the switch fixing portion is fixed to the adapter.

4. The ultrasonic treatment switch device according to claim 3, wherein the movement prevention member is formed of an elastically deformable resin material.

5. The ultrasonic treatment switch device according to claim 1, wherein the handpiece is formed substantially to be a pistol type;

the switch is provided with a button which is configured to be pressed with a forefinger of an operator and which causes the electric signal to be output from the power source so that the ultrasonic transducer generates the ultrasonic vibrations; and the adapter is provided with a hook portion to hook a finger except for the forefinger of the operator so that a movable range of the forefinger of the operator is increased.

6. The ultrasonic treatment switch device according to claim 1, wherein the handpiece is formed substantially to be a scissors-type; and the adapter is provided as an in-line type in which the adapter fixing portion is located in the vicinity of a tip side of a finger other than a thumb.

7. A medical device switch attachment system comprising:

an adapter detachably attached to a medical device gripped and used by a user; and a hand switch which is detachably attached to the adapter and which is disposed at a position within reach of the user while the medical device is gripped by the user and which switches the operation of the medical device, wherein the adapter comprises:

a common fixing seat to which the hand switch is attached; and a medical device attachment/detachment portion formed in conformity to the medical device.

8. The medical device switch attachment system according to claim 7, wherein the adapter is provided with a movement prevention member which prevents mutual movement when the hand switch is attached to the adapter.

9. The medical device switch attachment system according to claim 8, wherein the movement prevention member is formed of an elastically deformable resin material.

10. The medical device switch attachment system according to claim 7, wherein the medical device is formed substantially to be a pistol type;

the switch is provided with a button which is configured to be pressed with a forefinger of an operator and which causes an electric signal to be output from a power source to the medical device; and the adapter is provided with a hook portion to hook a finger except for the forefinger of the operator so that a movable range of the forefinger of the operator is increased.

11. The medical device switch attachment system according to claim 7, wherein the medical device is formed substantially to be a scissors-type; and the adapter is provided as an in-line type in which the fixing seat is located in the vicinity of a tip side of a finger other than a thumb.

* * * * *